United States Patent [19]
Slater et al.

[11] Patent Number: 6,066,083
[45] Date of Patent: May 23, 2000

[54] IMPLANTABLE BRACHYTHERAPY DEVICE HAVING AT LEAST PARTIAL DEACTIVATION CAPABILITY

[75] Inventors: Charles R. Slater, Fort Lauderdale; Scott L. Jahrmarkt, Miami Beach; Scott T. Smith, Miami; Kevin W. Smith, Coral Gables, all of Fla.

[73] Assignee: Syntheon LLC, Miami, Fla.

[21] Appl. No.: 09/200,698

[22] Filed: Nov. 27, 1998

[51] Int. Cl.[7] .................................................. A61M 36/12
[52] U.S. Cl. ..................................................... 600/8; 600/3
[58] Field of Search .............................................. 600/1–8

[56] References Cited

U.S. PATENT DOCUMENTS

| | | | |
|---|---|---|---|
| 3,351,049 | 11/1967 | Lawrence | 128/1.2 |
| 4,323,055 | 4/1982 | Kubiatowicz | 128/1.2 |
| 4,702,228 | 10/1987 | Russell, Jr. et al. | 128/1.2 |
| 4,784,116 | 11/1988 | Russell, Jr. et al. | 128/1.2 |
| 4,891,165 | 1/1990 | Suthanthiran | 252/633 |
| 5,342,283 | 8/1994 | Good | 600/8 |
| 5,405,309 | 4/1995 | Carden, Jr. | 600/3 |
| 5,503,614 | 4/1996 | Liprie | 600/7 |
| 5,713,828 | 2/1998 | Coniglione | 600/7 |

*Primary Examiner*—Cary O'Connor
*Assistant Examiner*—Catherine McPherson
*Attorney, Agent, or Firm*—David P. Gordon; David S. Jacobson; Thomas A. Gallagher

[57] ABSTRACT

An implantable brachytherapy device includes a biocompatible outer capsule containing a radiation shielding element and a radioactive isotope between the shielding element and the wall of the outer capsule. When the device is at body temperature, radiation is emitted by the isotope through the wall of the outer capsule. When a predetermined amount of energy is applied to the device, the shielding element is adapted to at least partially surround the isotope, and thereby at least partially prevent the transmission of radiation through the outer capsule.

34 Claims, 10 Drawing Sheets

IMPLANTABLE BRACHYTHERAPY DEVICE HAVING AT LEAST PARTIAL DEACTIVATION CAPABILITY

BACKGROUND OF THE INVENTION

1. Field of the Invention

The invention relates to implantable brachytherapy devices. More particularly, the invention relates to improved brachytherapy devices, also known as radioactive therapeutic seeds, for the treatment of oncological and other medical conditions.

2. State of the Art

Radioactive seed therapy is a well known and well accepted medical procedure for the treatment of various oncological and other medical conditions. Seed therapy, also known as interstitial brachytherapy typically involves the implantation of one to one hundred relatively small capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, in the case of prostatic interstitial brachytherapy they should be relatively small, approximately 0.025 inch in diameter and approximately 0.16 inch long so that they may be implanted into the prostate gland using minimally invasive instruments and techniques. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture", which are each incorporated by reference herein in their entireties. In addition, the art has been significantly advanced in co-owned U.S. Ser. Nos. 09/133,072, 09/133,081, and 09/133,082, which are hereby incorporated by reference herein in their entireties.

The Lawrence patent, which issued in 1967, describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which do not absorb X-rays. The isotope is coated on a rod shaped carrier made of similar X23 ray transparent (e.g. low Z) material and is placed inside the capsule cylinder which is then closed. The other patents each provide some improvement over the original Lawrence design.

Despite the fact that radioactive therapeutic seeds have been in use for over thirty years and despite the several significant improvements made in the seeds, many concerns still exist regarding the use of the seeds. The seeds contain isotopes with relatively short half lives, and are not intended to be removed from the body. As a result, the therapeutic dose is determined by the amount of isotope provided in the seeds and the half-life of the isotope. While the problem has not been previously identified, there are instances in which it is desirable after implantation to further control the amount of radiation emitted and/or length of time which radiation is emitted by the seeds to the locus of implantation in the patient.

The ability, after implantation, to control the amount of radiation emitted by the seed is important for several reasons. First, the physician may desire to provide a high therapeutic dose of radiation for a relatively short period of time, and the decay period until the seed is considered ineffective as a radiation source may be deemed too long. Second, the implanted seed may be determined, e.g., via radiography, to have been implanted in a location at which radiation treatment is not desirable. Third, radiation from seeds implanted for treatment of prostatic cancer can cause irritation of the urethra and rectum. The physician may decide at some point in the treatment that the benefits of further radiation treatment at the prostate are outweighed by patient discomfort. Fourth, as sometimes occurs with the seeds, one or more seeds may be passed by the patient in a bowel movement or through the urethra during urination. The patient may collect the seed, but does not have a manner of safely storing or disposing the highly radioactive seed.

None of the art addresses any manner of deactivating or reducing the level of amount of radiation emitted by the seed after the seed is implanted in the patient.

SUMMARY OF THE INVENTION

It is therefore an object of the invention to provide radioactive therapeutic seeds which are at least partially deactivatable after implantation to reduce the level of radioactivity emitted therefrom.

It is also an object of the invention to provide radioactive therapeutic seeds which are substantially completely deactivatable after implantation to prevent radiation to be emitted therefrom.

In accord with these objects which will be discussed in detail below, the radioactive brachytherapy seeds of the present invention generally include an outer capsule containing a radioactive isotope, and a substantially radiopaque shielding element which upon implantation does not substantially obstruct radiation emission by the isotope, but after implantation can still be controlled to at least partially surround the radioactive isotope and thereby at least partially reduce the level of radiation emitted by the seed. For purposes herein, "radiopaque" refers to the property of having a relatively "high Z" value, and the terms "radiopaque" and "high Z" are used interchangeably herein.

Various embodiments of the radiopaque shielding element are provided. In a first embodiment, a radiopaque material, such as a bismuth alloy, indium alloy, or solder eutectic, may be heated and forced to flow, by pressurized fluid or mechanical means, about the isotope and substantially prevent radiation emission by the seed. In a second embodiment, an elastic or heat shrinkable casing is stretched over a radiopaque material and the isotope is deposited on the casing. When the radiopaque material is heated to a melted state, the force of the casing on the radiopaque material moves the radiopaque material out of the casing, the casing collapses, and the radiopaque material surrounds the isotope on the casing to reduce or eliminate radiation emission from the seed. In a third embodiment, a flowable radiopaque element is retained by a removable barrier. The barrier may be removed by melting (e.g., a wax stopper barrier), breaking, or by a valve mechanism, and a pressurizing agent then forces the flowable radiopaque element to surround the isotope. In a fourth embodiment, a first member is provided with regions upon which the isotope is deposited. The first member is disposed within a second member which includes one or more substantially radiotransparent regions through which the radiation may pass and one more substantially radiopaque regions. The radiotransparent regions are positioned over the radioactive isotope regions. The first member may be controlled to move relative to the second member, e.g., by heat, vibration, or inertia, such that the radiopaque regions are positioned over the isotope and substantially block the emission of radiation of the isotope through the outer capsule. In a fifth embodiment, a radiopaque shape memory alloy coil element is provided over an elongate element having an isotope deposited on a portion thereof. The rings of the coil are in a naturally expanded state over the elongate element to permit radiation to be emitted through the rings of the coil and out of the outer capsule. The coil is trained to form a shape which substantially blocks the isotope when heated. In a sixth embodiment, a plurality of radiopaque shape memory alloy elements are provided, with each element having a portion on which the isotope is deposited. The portions provided with the isotope are oriented for emitting radiation through the outer capsule. The elements are trained such that when they are heated, the elements change shape (or otherwise move) to substantially surround the portions provided with the isotope and thereby substantially prevent the emission of radiation.

It will be appreciated that in embodiments utilizing heat to "deactivate" the seed, the heat may be provided by hot water, microwave technology, or other radiating means provided at or near the seed implant site. Additional means for substantially "deactivating" or at least reducing seed radioactivity may also be used.

It will be further appreciated that the ability to control the amount of radiation emitted by the seed enables the physician to "turn off" the seed or at least reduce the radiation emitted by the seed when desired; i.e., upon the application of a predetermined amount of energy. In addition, with respect to heat "deactivatable" seeds, should the patient recover a 'passed' seed, the patient can safely "deactivate" the seed by immersing the seed in hot water.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
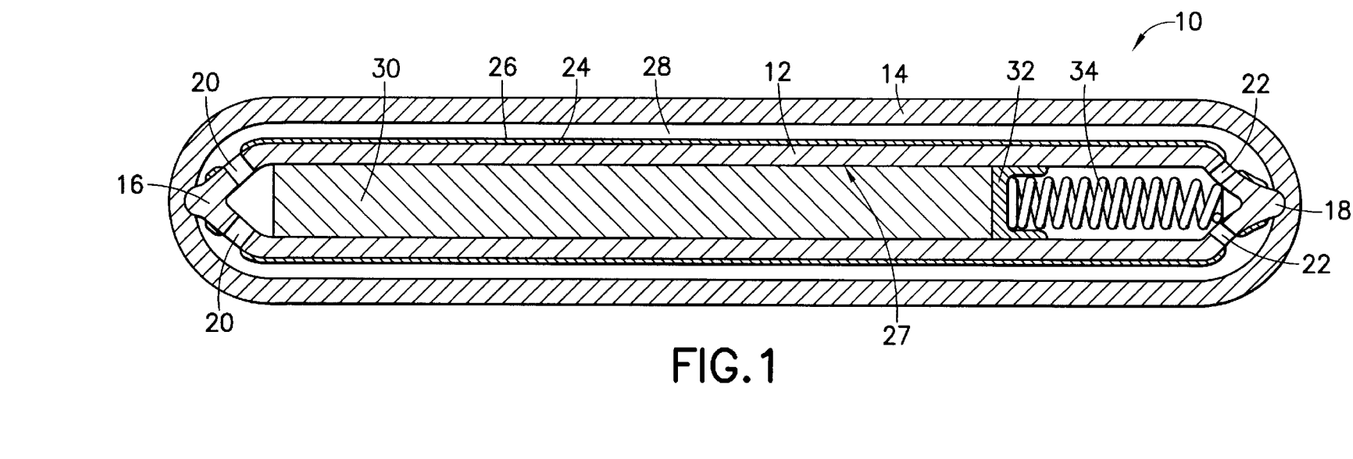
FIG. 1 is a section view of a first embodiment of an at least partially deactivatable brachytherapy seed in an "active" configuration.

Referring now to FIG. 1, a brachytherapy seed 10 according to the invention is shown. The seed 10 includes an inner capsule 12, preferably made from aluminum, provided within a biocompatible outer capsule 14, preferably made from titanium, aluminum, or stainless steel. The outer capsule 14 may be sealed closed about the inner capsule 12 according to any method known in the art, including the methods disclosed in previously incorporated U.S. Ser. No. 09/133,081. For treatment of the prostate, the outer capsule preferably has a diameter of less than 0.10 inches, and more typically a diameter of less than 0.050 inches, and preferably has a length of less than 0.50 inches, and more typically a length of less than 0.16 inches.

Figure 1A:
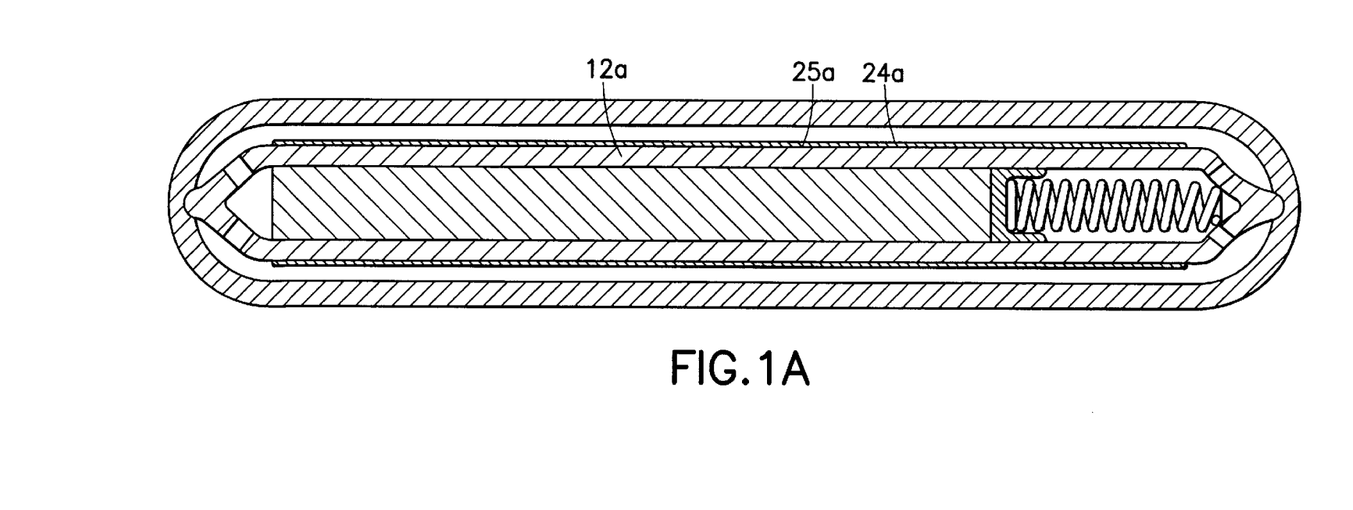
FIG. 1A is a section view of an alternate first embodiment of an at least partially deactivatable brachytherapy seed in an "active" configuration.

The inner capsule 12 includes first and second ends 16, 18, and respective first and second openings 20, 22 at the respective ends. The inner capsule 12 is preferably coaxially held within the outer capsule 14 at the first and second ends 16, 18 of the inner capsule 12, such that a preferably uniform space 28 is provided between the inner and outer capsules. The inner capsule 12 includes an exterior surface 24 provided with a radioactive isotope 26, e.g., I-125, Pd-103, Cs-131, Xe-133, and Yt-169, which emit low energy X-rays and which have relatively short half-lives. Alternatively, referring to FIG. 1A, the radioactive isotope 24a is provided on a sleeve 25a extended over the inner capsule 12a. Furthermore, turning back to FIG. 1, while not preferred, the radioactive isotope may be provided to the interior surface 27 of the inner capsule 12 (either by deposition thereon or an internal sleeve provided thereagainst).

At the first end 16, the inner capsule 12 is at least partially filled with a radiopaque material 30 having a low melting point, e.g., an indium alloy, a bismuth alloy, or a solder or other eutectic, which is in solid form when the seed 10 is emitting radiation or "active"; i.e., the state of the material 30 at body temperature is solid. For purposes herein it will be appreciated that "radiopaque" refers to the material property of a relatively high Z value such that the material substantially blocks the transmission of radiation therethrough. It will be appreciated that the radiopaque material 30 serves as a marker for fluoroscopic viewing of the implanted seeds and, as described below, can be melted at a temperature safe to the patient to shield the radioactive isotope and thereby reduce radiation emission by seed. The radiopaque material 30 preferably has a low melting point; e.g., approximately 105° or 110° up to approximately 160°. A piston 32 is provided in the inner capsule 12 and, upon the liquefication of the radiopaque material, is capable of moving, e.g., by sliding, along a length of the inner capsule. A spring element 34 is provided between the second end 18 of the inner capsule 12 and the piston 32, forcing the piston against the radiopaque material. When the brachytherapy seed 10 is implanted, the isotope 26 on the exterior surface 24 of the inner 12 capsule emits radiation through the outer capsule 14 to the implant site.

Figure 2:
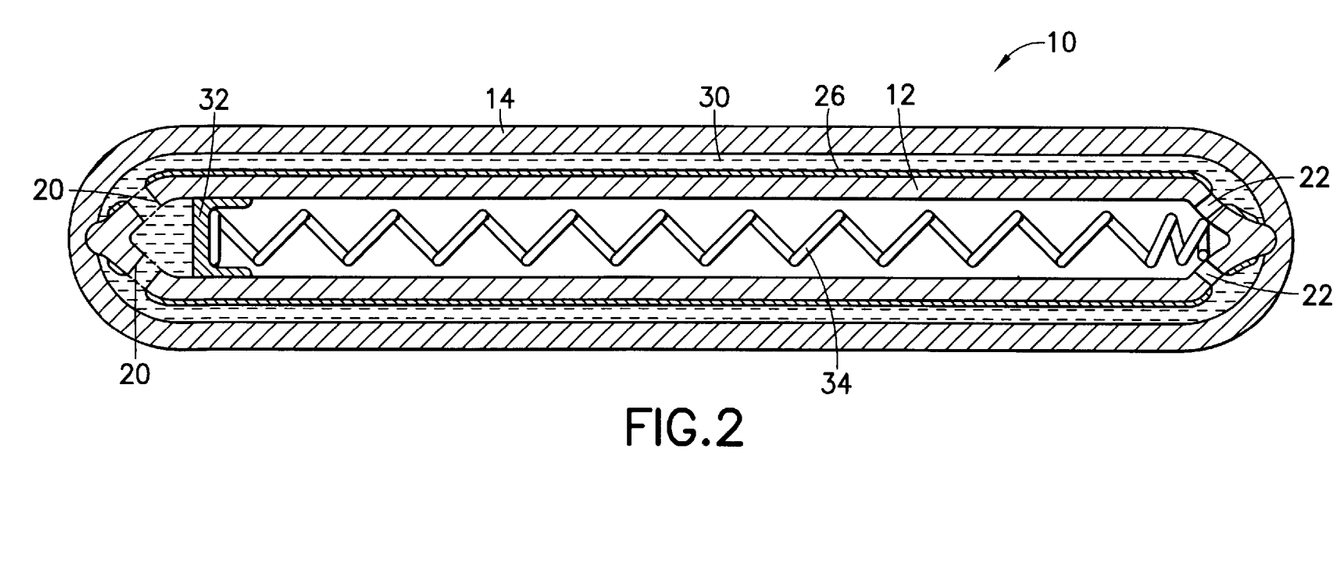
FIG. 2 is a section view of the first embodiment of an at least partially deactivatable brachytherapy seed in a "deactivated" configuration.

Turning now to FIG. 2, when it is desired to reduce radiation emission by the seed, that is, "deactivate" the seed, the seed may be "deactivated" by applying heat which causes the radiopaque material 30 to melt. The heat may be applied, for example, by hot water provided in the urethra, by microwave radiation, or by other types of radiation. The spring element 34 provides force against the piston 32 which, in turn, forces the radiopaque material 30 out of the first openings 20 and into the space 28 between the inner and outer capsules 12, 14. The second openings 22 permit gas trapped between the inner and outer capsules 12, 14 to be moved into the inner capsule 12 as the radiopaque material 30 flows and surrounds the inner capsule 12 and isotope 26 deposited thereon. It will also be appreciated that second openings 22 are not required if the outer capsule 14 is evacuated during manufacture. Once the radiopaque material has surrounded the inner capsule, the capsule is substantially "deactivated" (i.e., no radiation escapes the seed 10) or at least partially "deactivated" (where encapsulation of the inner capsule by the radiopaque material is at least partial, yet incomplete).

Figure 3:
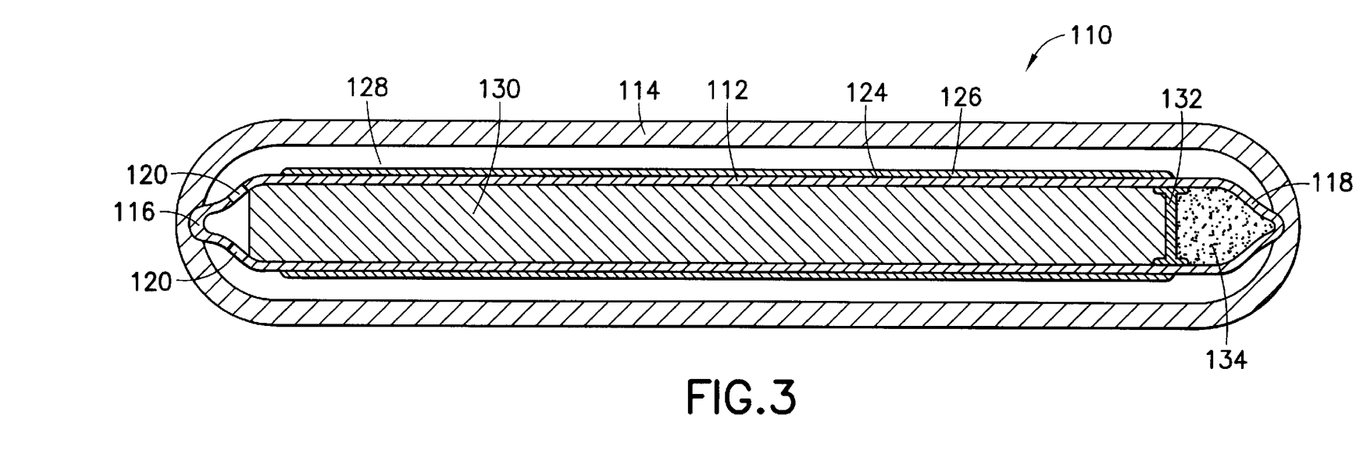
FIGS. 3 and 4 are section views of a second embodiment of an at least partially deactivatable brachytherapy seed in "active" and "deactivated" seed configurations, respectively.

Referring now to FIG. 3, according to a second embodiment of the invention, substantially similar to the first embodiment, the brachytherapy seed 110 includes an inner capsule (or inner cylinder) 112 provided within an outer capsule 114. The inner capsule 112 includes first and second ends 116, 118, and one or more openings 120 at the first end. A radioactive isotope 126 is either deposited on the exterior surface 124 of the inner capsule 112 (as shown), provided on a sleeve extended over the inner capsule (not shown), or provided against the interior surface of the inner capsule (not shown).

At the first end 116, the inner capsule is at least partially filled with a radiopaque material 130. A piston 132 is provided in the inner capsule 112 against the solid radiopaque material 130, and a pressurized fluid (liquid or gas) 134 is provided between the piston 132 and the second end 118 of the inner capsule urging the piston toward the first end 116.

Figure 4:
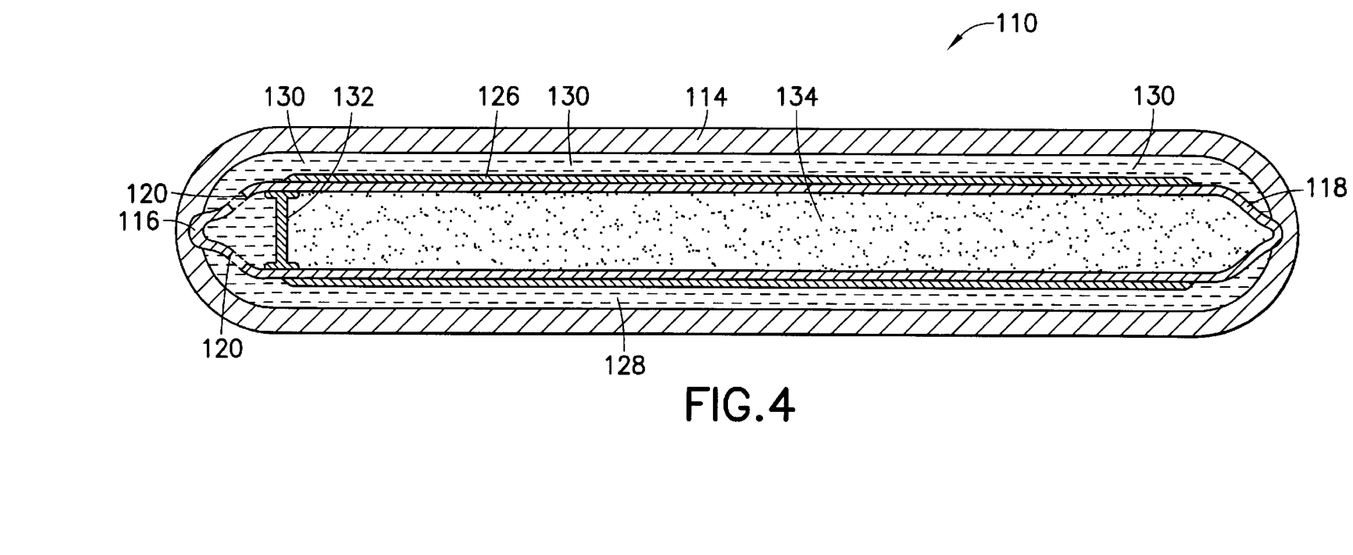

Turning now to FIG. 4, the seed 110 may be "deactivated" by applying heat energy which causes the radiopaque material 130 to melt. The pressurized fluid 134 then moves the piston 132 away from the second end 118, and the piston 132 moves the melted radiopaque material 130 through the first openings 120 in the inner capsule into the space 128 between the inner capsule 112 and the outer capsule 114. Flow of the radiopaque material 130 such that the radiopaque material surrounds the inner capsule 112 and isotope 126 located thereon (or thereagainst) is thereby facilitated.

Figure 5:
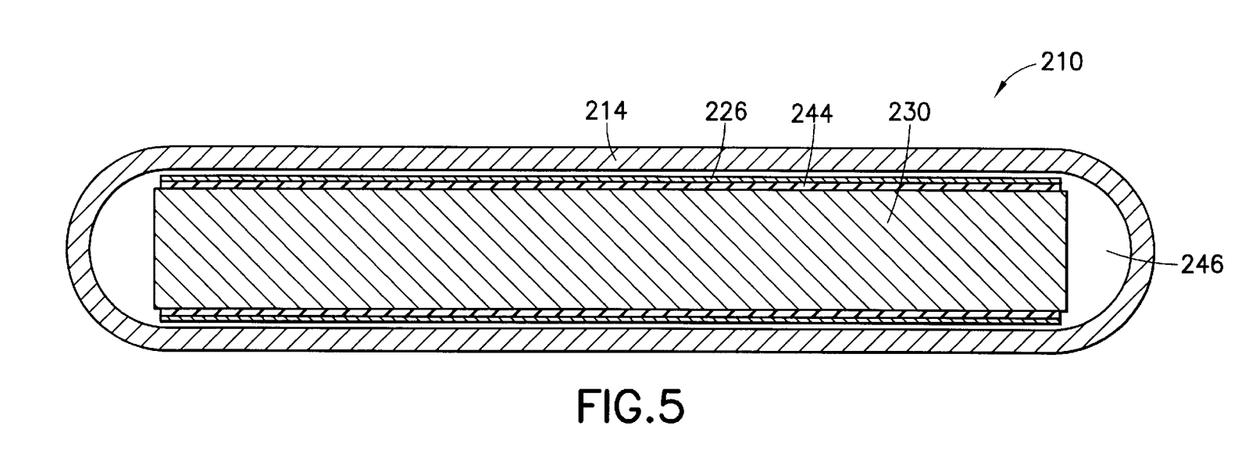
FIGS. 5 and 6 are section views of a third embodiment of an at least partially deactivatable brachytherapy seed in "active" and "deactivated" seed configurations, respectively.

Referring now to FIG. 5, according to a third embodiment of the invention, the brachytherapy seed 210 includes a capsule 214 having therein a metal rod 230 formed from a low melting point radiopaque material which is provided with an elastic cover 244, e.g, latex, stretched thereover. Alternatively, the cover may be made from a heat shrinkable material. As yet another alternative, the metal rod may be replaced by a rod formed from radiopaque metal flakes or fragments provided in a wax carrier. The cover 244 is provided with a radioactive isotope 226 thereon. The rod 230 and cover 244 preferably substantially fill the interior 246 of the capsule 214.

Figure 6:
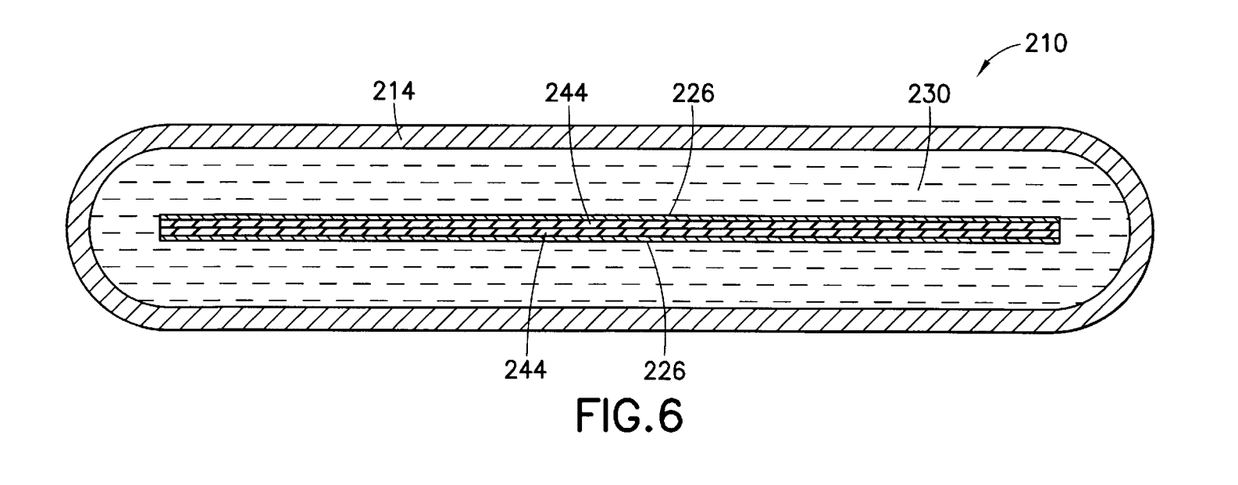

Turning now to FIG. 6, when the capsule 214 is heated, the rod 230 liquefies and the cover 244 collapses inward to force the radiopaque material out from within the cover. The radiopaque material 230 (or wax with radiopaque flakes) thereby surrounds the collapsed cover 244, with isotope 226 deposited thereon, and prevents, or at least substantially prevents, the emission of radiation by the seed 210.

Figure 7:
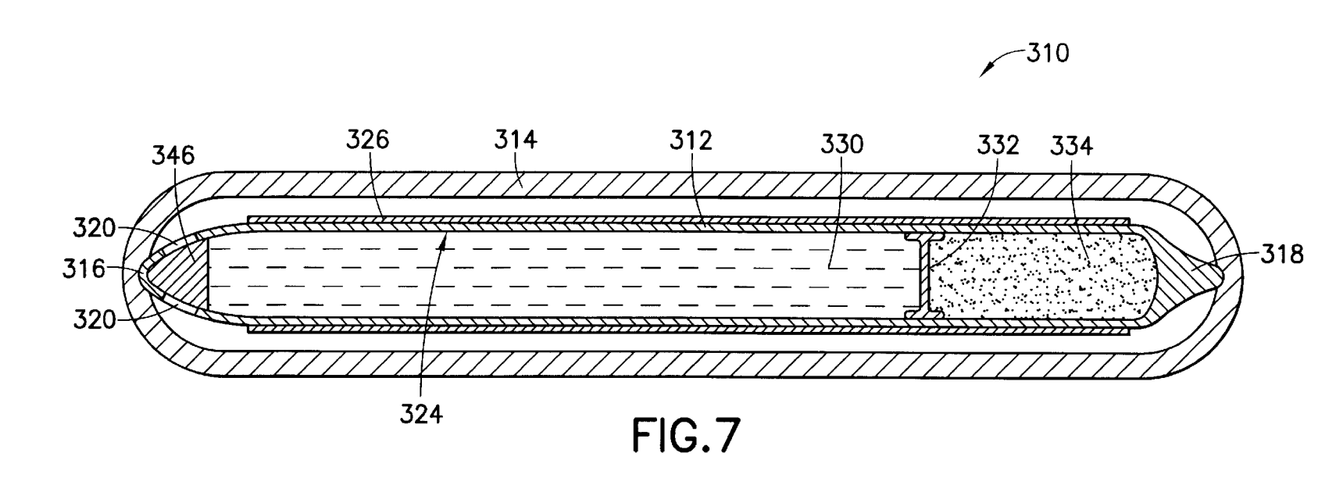
FIGS. 7 and 8 are section views of a fourth embodiment of an at least partially deactivatable brachytherapy seed in "active" and "deactivated" seed configurations, respectively.

Referring now to FIG. 7, according to a fourth embodiment of the invention, the brachytherapy seed 310 includes an inner capsule 312 provided within an outer capsule 314. The inner capsule 312 includes first and second ends 316, 318. The first end 316 includes openings 320. A radioactive isotope 326 is deposited on a surface 324 of the inner capsule 312. The inner capsule is preferably coaxially held within the outer capsule.

The inner capsule 312 is partially filled with a high Z material 330 which is liquid at body temperature, e.g., mercury. The inner capsule is also provided with a pressurized fluid (gas or liquid) 334. A piston 332 separates the high Z material 330 and the pressurized fluid 334. The liquid material 330 is contained within the inner capsule by a wax plug 346 or the like, which is substantially solid at body temperature and which blocks the passage of the liquid high Z material 330 through the openings 320 at the first end 316 of the inner capsule 312.

Figure 8:
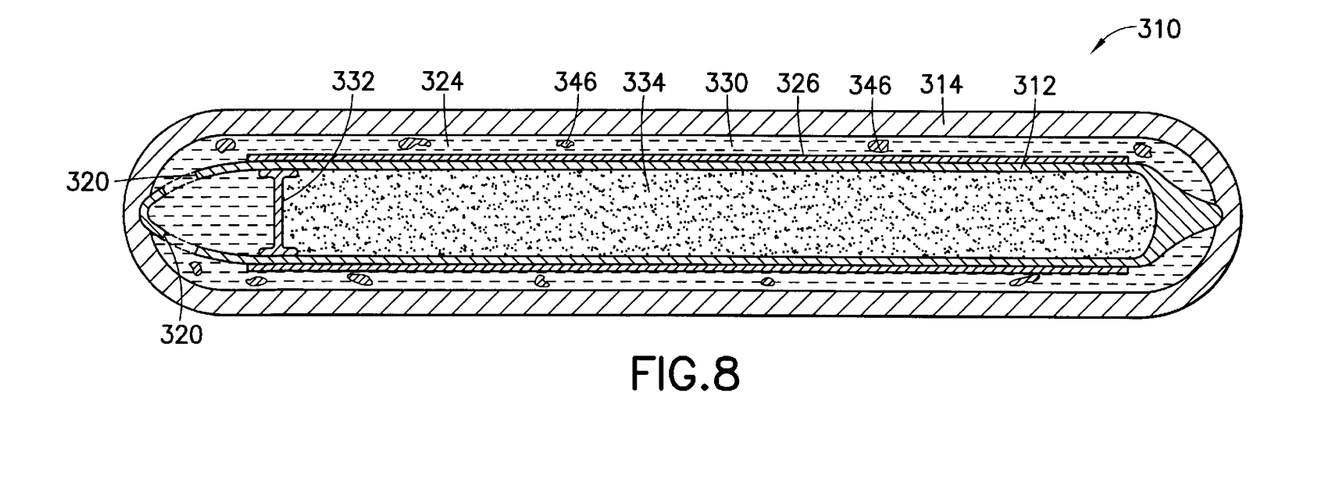

Turning now to FIG. 8, when the seed 310 is heated, the plug 346 is melted and the pressurized fluid 334 forces the melted plug 346 and radiopaque material 330 to exit the openings 320 at the first end 316 of the inner capsule 312 and surround the inner capsule and radioactive isotope 326 thereon.

It will be appreciated that as an alternative to a wax plug 346 or the like, a frangible disc or valve may be utilized to retain the liquid high Z material. The disc or valve may be operated via heat or mechanical means to controllably permit the liquid high Z material to flow out of the inner capsule. Furthermore, as an alternative to the liquid high Z material 330 and plug 346, both may be replaced with an insert provided in the inner capsule made from high Z particle carried in a wax. When the seed is heated, the wax melts and, along with the particles, is forced, from the inner capsule by the pressurized gas such that the high Z particles surround the isotope and substantially reduce the radiation emitted by the seed.

Figure 9:
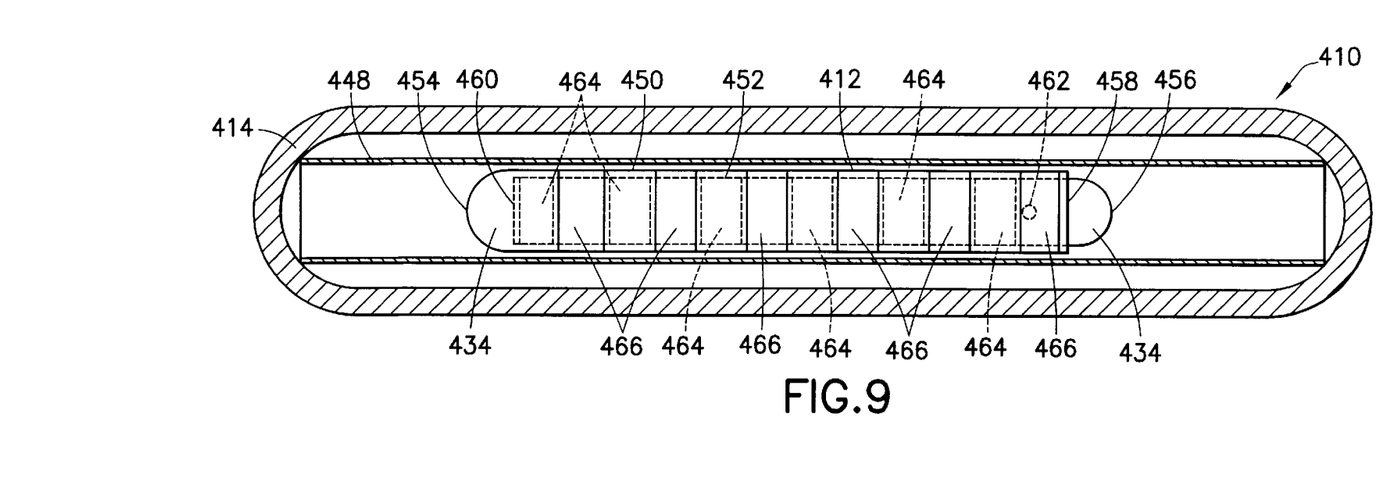
FIGS. 9 and 10 are section views of a fifth embodiment of an at least partially deactivatable brachytherapy seed in "active" and "deactivated" seed configurations, respectively.

Referring now to FIG. 9, according to a fifth embodiment of the invention, the brachytherapy seed 410 includes an inner capsule 412 provided within an outer capsule 414. The inner capsule 412 is preferably held substantially coaxial within the outer capsule by a gas permeable tube 448, e.g., a mesh or perforate tube formed of metal or plastic. The inner capsule 412 is comprised of first and second preferably substantially tubular components 450, 452, each having a closed end 454, 456, respectively, and an open end 458, 460, respectively. The open end 458 of the first component 450 is sized to receive therein at least the open end 460 and a portion of the second component 452. The first and second components 450, 452 together thereby form a "closed" inner capsule 412. At least one of the first and second components is provided with a hole 462 which is blocked by the other of the first and second components when the inner capsule is in the "closed" configuration. A gas 434 is provided in the closed inner capsule 412.

The first component 450, and optionally also the second component 452, are made from a substantially low Z material. The second component 452 is provided with a plurality of preferably circumferential bands 464 of a radioactive isotope material, while the first component 450 is provided with a plurality of preferably circumferential bands 466 of a high Z material. The first and second components are fit together such that along the length of the inner capsule 412 a series of alternating bands of radioactive isotope material and high Z material are provided. The bands 466 of high z material do not significantly affect the emission of radiation at the isotope bands 464 by the seed.

Figure 10:
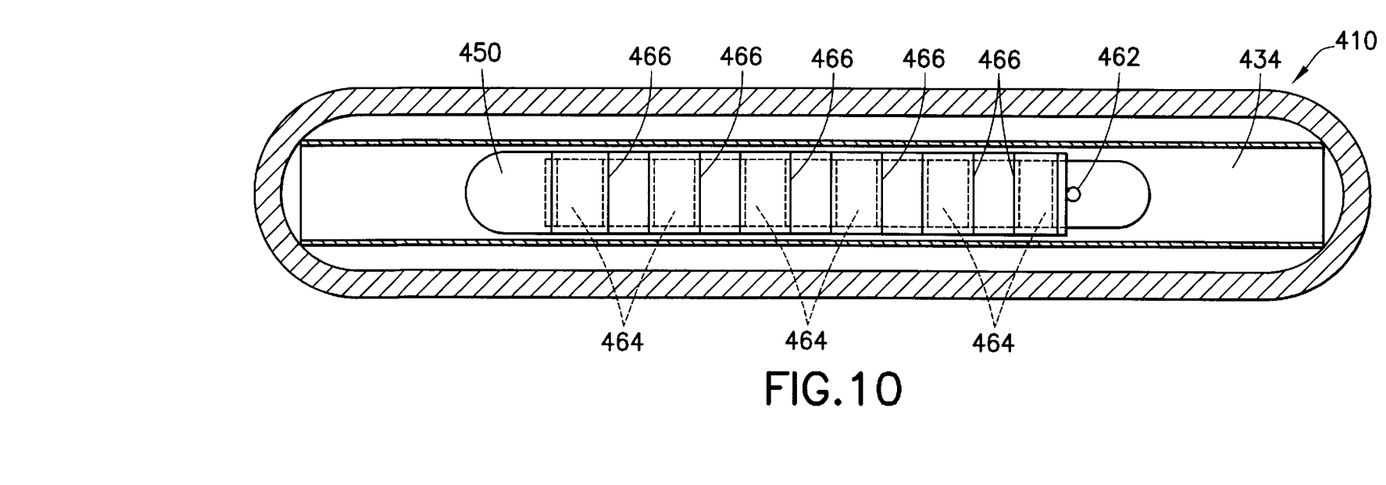

Turning now to FIG. 10, when the seed 410 is heated, the gas 434 within the inner capsule 412 increases in pressure and forces the second component axially away from the first component such that the volume of the inner capsule increases. As the first and second components 450, 452 move axially apart, the hole 462 becomes exposed which equalizes the pressure between the interior of the inner capsule 412 and the interior of the outer capsule 414, terminating the axial movement. The hole 462 is preferably positioned such that movement is terminated with the high Z bands 466 of the first component 450 substantially blocking radiation transmission by the radioactive isotope bands 464 of the second component 452.

It will be appreciated that the other means may be used to move the first and second components 450, 452 relative to each other. For example, a one-way inertial system or an electromagnetic system may be used. In addition, it will be appreciated that the inner capsule 412 may be configured such that the high Z bands 466 only partially block the radioactive isotope bands 464; i.e., that the seed 410 may be partially deactivated to provide only, for example, ten to ninety percent of the radiation emitted by the seed prior to partial deactivation.

Figure 11:
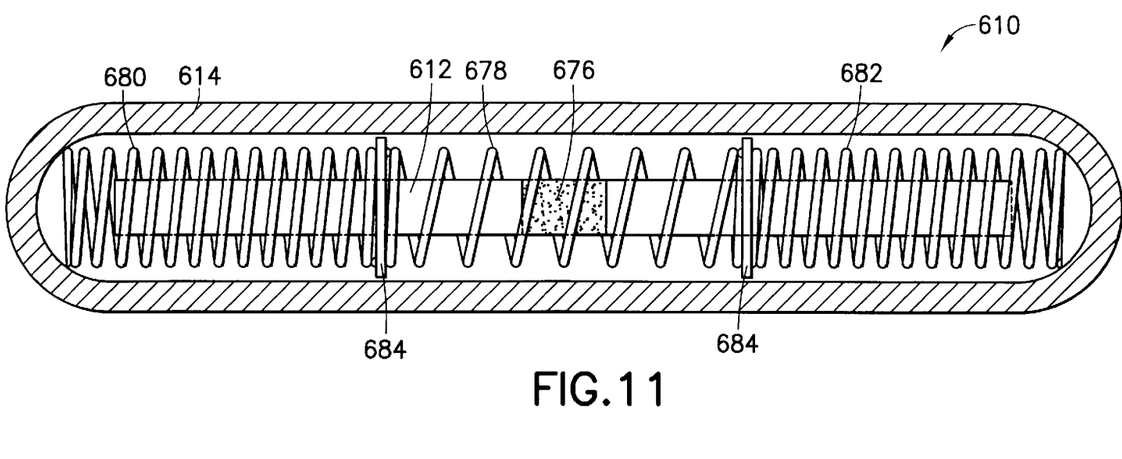
FIGS. 11 and 12 are section views of a sixth embodiment of an at least partially deactivatable brachytherapy seed in "active" and "deactivated" seed configurations, respectively.

Referring now to FIG. 11, according to a sixth embodiment of the invention, a brachytherapy seed 610 includes an inner wire 612 provided with a circumferential band 676 of radioactive isotope material. A shape memory spring coil 678 is positioned centrally over the coil. The shape memory coil 678 is preferably made from a relatively high Z material, e.g., Nitinol, and is trained to contract when subject to a predetermined amount of heat. Second and third spring coils 680, 682 are positioned on either side of the shape memory coil 678. Washers 684 may be positioned between each of the coils 678, 680, 682 to maintain the separation of the coils; i.e., to prevent the coils from entangling and to better axially direct their spring forces. The wire 612 and coils 678, 680, 682 are provided in an outer capsule 614. The radioactive isotope 676 emits radiation between the rings of the shape memory coil 678 and through the outer capsule 614.

Figure 12:
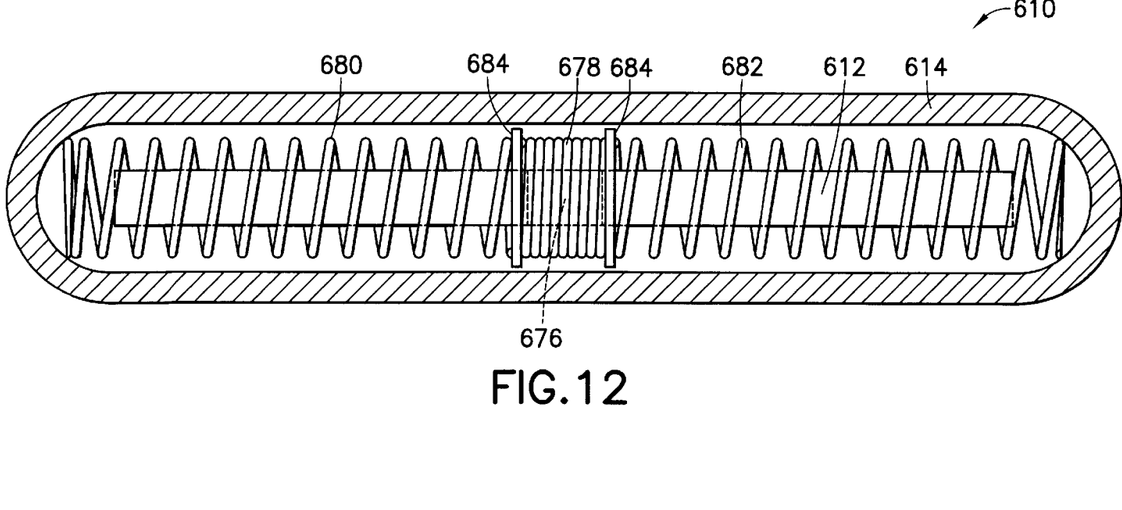

Turning now to FIG. 12, when the seed 610 is subject to a predetermined amount of heat, the shape memory coil 678 contracts to substantially surround the band 676 of isotope. The shape memory coil spring 678 is held centered over the band by the second and third spring coils 680, 682 which apply substantially equal but opposite forces against the shape memory coil 678.

Figure 13:
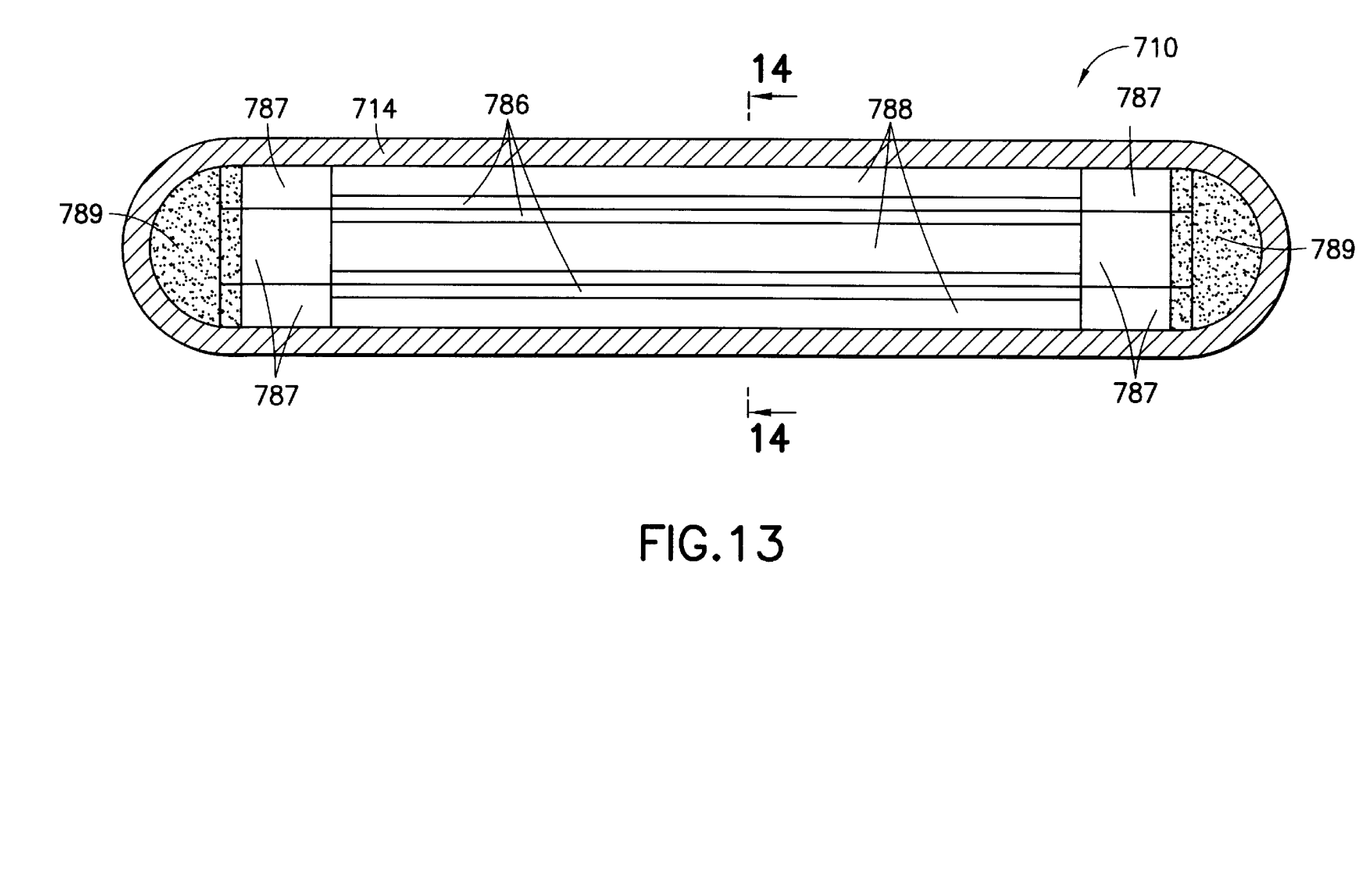
FIG. 13 is a longitudinal section view of a seventh embodiment of an at least partially deactivatable brachytherapy seed in an "active" seed configuration.
Figure 14:
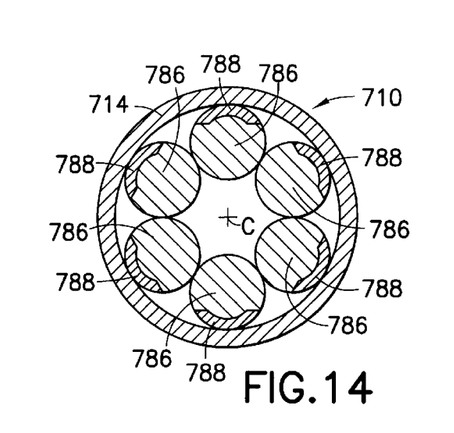
FIG. 14 is a cross section through line 14—14 of FIG. 13.

Referring now to FIGS. 13 and 14, according to a seventh embodiment of the invention, a brachytherapy seed 710 includes a relatively radiotranslucent capsule 714 provided with preferably six rods 786 oriented longitudinally in the capsule 714. The rods 786 are made from a shape memory material which preferably is substantially radiopaque, e.g., a nickel titanium alloy. Each end of each rod is provided with a twisted portion 787. In addition, the ends of the rods are secured, e.g., by glue 789, in the outer capsule 714. When the rods are subject to heat energy, the rods are adapted to untwist at their respective twisted portions 787 about their respective axes. The rods 786 are each provided with a longitudinal stripe 788 (preferably extending about 600 to 1200 about the circumference of the rods) of a radioactive isotope along a portion of their length, and preferably oriented in the capsule 714 such that the stripe 788 of each is directed radially outward from the center C of the capsule.

Figure 15:
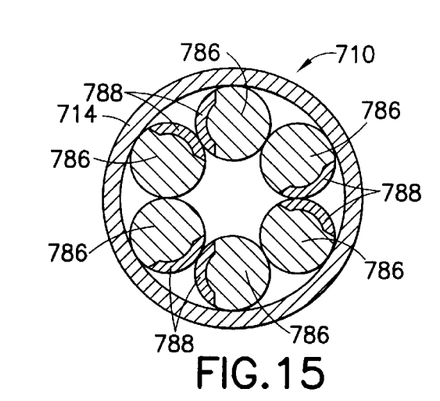
FIGS. 15 and 16 are cross section views of the seventh embodiment of in "transitional" and "deactivated" seed configurations, respectively.
Figure 16:
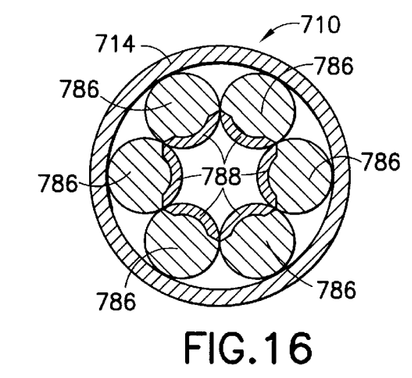

Turning now to FIG. 15, when subject to heat energy, the shape memory rods 786 within the seed 710 twist (or rotate) along their axes. The rods 786 are preferably oriented such that adjacent rods rotate in opposite directions. In this manner, a stripe 788 on one rod rotates against a stripe on an adjacent rod, preventing the isotope from being transferred to a 'clean' portion of the rod. Turning now to FIG. 16, the rods 786 are trained to rotate preferably 180° about their respective axes. As a result, the isotope stripe 788 along each of the rods 786 is eventually directed radially inward, and the high Z material of the rods around the isotope stripes 788 prevents the emission of radiation from the seed 710.

It will be appreciated that the rods 786 are not required to be substantially radiopaque and that alternatively, or additionally, the rods may be circumferentially deposited with a relatively high Z material along their length at least diametrically opposite the longitudinal stripes of radioactive isotopes, and preferably at all locations on the rods other than on the stripes 788. Furthermore, it will be appreciated that fewer than six or more than six rods may be provided in the capsule. Moreover, a central rod may also be used to maintain the rods in the desired spaced apart configuration; i.e., such that the rods together form a generally circular cross section.

Figure 17:
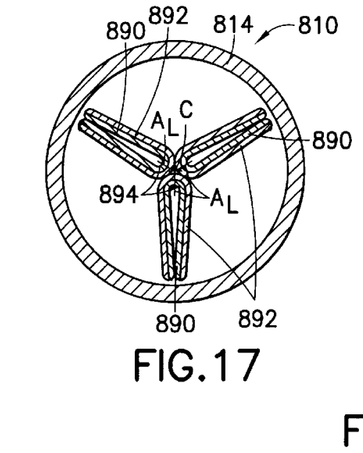
FIGS. 17 through 20 are cross section views of an eighth embodiment of an at least partially deactivatable brachytherapy seed in "active", "transitional", "substantially deactivated", and "deactivated" seed configurations, respectively.

Referring now to FIG. 17, according to an eighth embodiment of the invention, a brachytherapy seed 810 includes a relatively radiotranslucent capsule 814 provided with preferably three elongate shape memory strips 890 positioned lengthwise in the capsule 814. It will be appreciated that two or four or more strips 890 may also be used. The strips are preferably made from a Nitinol and are also preferably coated with a high Z material, e.g., gold or a heavy metal, on one side and with a radioactive isotope 892 or radioactive isotope carrier on the side opposite the high Z material coating. The strips 890 are each bent along their longitudinal axis $A_L$ such that the isotope is provided on an external surface of the bent strip 890. The strips 890 are preferably positioned in the capsule at 120° relative separation, with the bend 894 of each strip located at or near the radial center C of the capsule 814. Optionally, the strips 890 may be coupled together at the bends 894, e.g., by soldering, to maintain the strips in the desired relative separation. The isotope 892 on the strips 890 emits radiation through the seed capsule 814.

Figure 18:
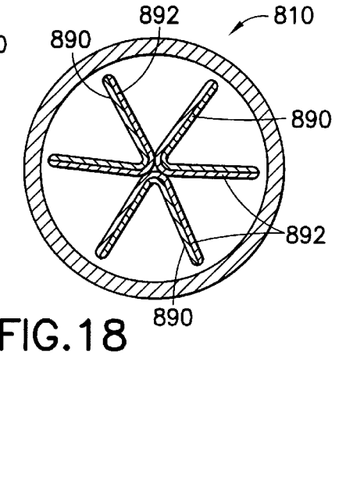
Figure 19:
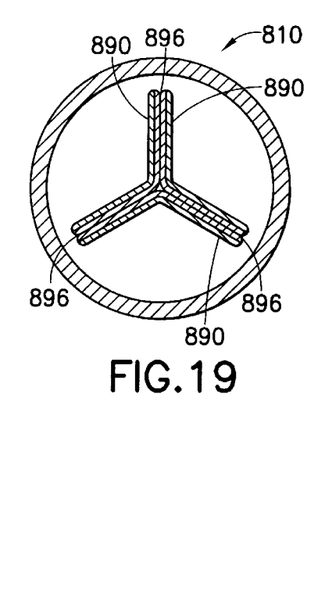
Figure 20:
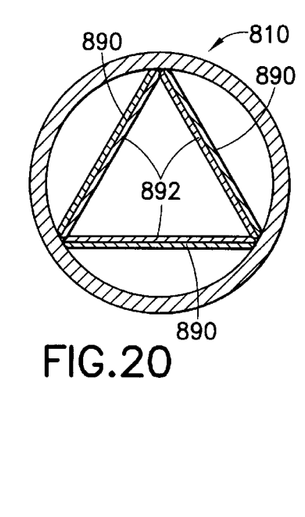

The shape memory strips 890 are trained to open from their bent configuration when heated. As shown in FIGS. 18 and 19, when heat is applied to the seed, the strips 890 unfold from their bent configuration such that eventually the high Z material of the strips substantially blocks the emission of radiation from the isotope 892 (radiation being emitted only from between the ends of the strips, at 896) and at least partially "deactivates" the seed 810. Turning to FIG. 20, in addition, if the strips 890 are not coupled at their respective bends 894, the strips may be trained such that each opens to a substantially planar configuration, and together the strips 890 form a triangle which substantially surrounds the isotope and substantially "deactivates" the seed.

Figure 21:
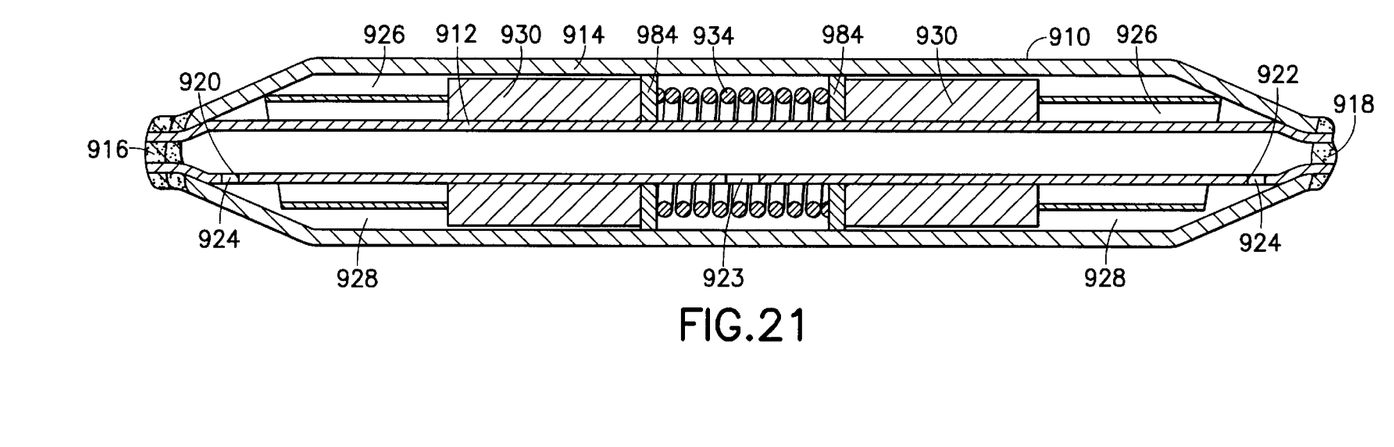
FIGS. 21 and 22 are section views of a ninth embodiment of an at least partially deactivatable brachytherapy seed in "active" and "deactivated" seed configurations, respectively.

Referring now to FIG. 21, according to a ninth embodiment of the invention, the brachytherapy seed 910 includes an inner capsule 912 co-axially positioned within an outer capsule 914. The inner capsule 912 includes first and second ends 916, 918 having respective openings 920, 922, and preferably a central opening 923. The openings 920, 922 provided at the ends of the inner capsule 912 are preferably arranged as bubble point discriminators 924 which are gas permeable but not liquid permeable. Two tubular radioactive elements 926 are provided between the inner and outer capsules 912, 914, and are sized and shaped (e.g., with angled ends) to provide a "flow" space 928 between the elements 926 and the outer capsule 914. A spring element 934 is provided over the inner capsule 912 and centrally located, and washer elements 984 are preferably provided lateral the spring 934. Between each washer element 984 and a respective one of the radioactive elements 926, a meltable radiopaque element 930 is provided.

Figure 22:
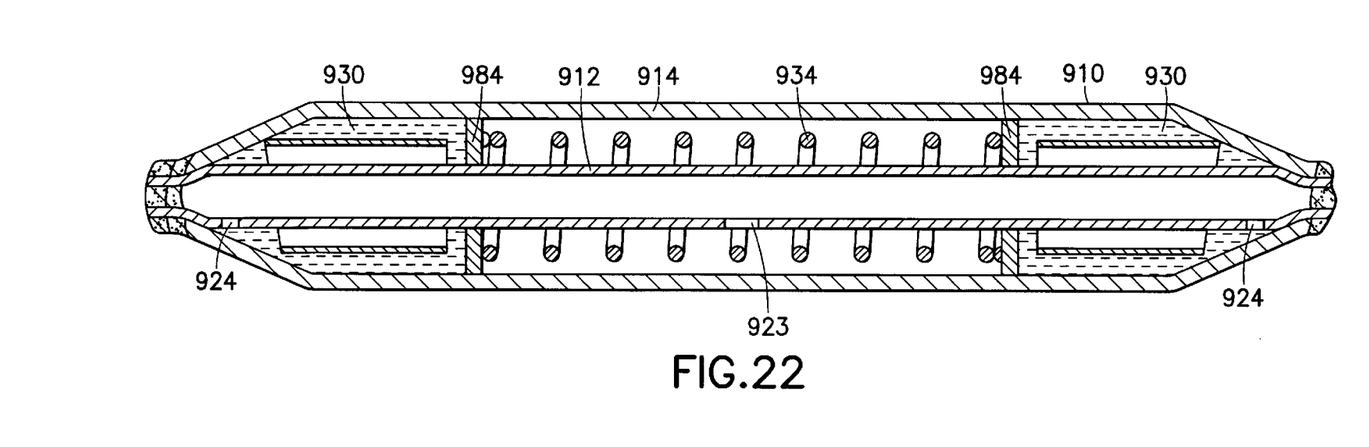

Turning now to FIG. 22, when the seed 910 is heated, the radiopaque elements 930 are melted and the spring 934 forces the radiopaque material 930 over the radioactive elements 926. Gas, e.g., formerly located in the space now occupied by the radiopaque material 930 passes through the bubble point discriminators 924 into the inner capsule 912, and may exit the inner capsule at the central opening 923 into the space between the two washer elements 984.

There have been described and illustrated herein several embodiments of a deactivatable radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciate that certain features of one embodiment may be combined with features of another embodiment to provide yet additional embodiments. Also, while hot water is disclosed as a heat source for "deactivating" many of the embodiment of the "deactivatable" seeds, it will be appreciated that microwave technology or other forms of radiated energy provided at or near the seed implant site may also be used to generate sufficient heat. Furthermore, it will be appreciated that other types of energy can be used to trigger partial or complete seed "deactivation". For example, mechanical, electromagnetic, and piezoelectric can also be used. Moreover, while a radioactive isotope having a relatively short half-lives is desired, it will be appreciated that "deactivation" capability permits the use of isotopes having relatively longer half-lives. In addition, while particular dimensions have been disclosed for the seeds, it will be appreciated that other dimensions may be likewise be used depending on the particular application of the seed; i.e., its locus of implantation. Also, it will be appreciated that the terms "radiotransparent", "radiotranslucent", and "low Z" are intended to have the same meaning for purpose of the prior description and in the construction of the claims which follow. It will therefore be appreciated by those skilled in the art that yet other modifications could be made to the provided invention without deviating from its spirit and scope as so claimed.

What is claimed is:

1. An implantable brachytherapy device, comprising:
   a) a first container;
   b) radioactive means for emitting radiation out of said first container; and
   c) activatable radiation reduction means in said container for at least partially reducing the amount of radiation emitted out of said first container in response to an application of an amount of energy to said device.

2. An implantable brachytherapy device according to claim 1, wherein:
   said radiation reduction means completely prevents the emission of radiation out of said first container.

3. An implantable brachytherapy device according to claim 1, wherein:
   said first container has a diameter of less than 0.10 inches and a length of less than 0.50 inches.

4. An implantable brachytherapy device according to claim 1, further comprising:
   d) a inner second container inside said first container, wherein:
      said radioactive means and said radiation reduction means are located between said second container and said first container prior to activation of said radiation reduction means.

5. An implantable brachytherapy device according to claim 4, wherein:
   when said radiation reduction means is activated, said radiation reduction means at least partially surrounds said radioactive means.

6. An implantable brachytherapy device, comprising:
   a) a container having a wall adapted for the transmission of radiation therethrough;
   b) a radioactive isotope which emits radiation and which is provided in said container; and
   c) an activatable shield provided in said container for reducing the amount of radiation transmitted through said container when an amount of energy is applied to said device.

7. An implantable brachytherapy device according to claim 6, wherein:
   said amount of energy is heat at a temperature above body temperature.

8. An implantable brachytherapy device according to claim 6, further comprising:
   d) a member having a portion upon which said isotope is provided,
      wherein said activatable shield is a substantially radiopaque shape memory coil extended over said member and adapted to contract and substantially cover said portion of said member on which said isotope is provided when said energy is applied to said coil.

9. An implantable brachytherapy device according to claim 6, further comprising:
   e) a first tubular member with a first diameter having a first closed end and a first open end, said first tubular member having at least one portion provided with said radioactive isotope, and
   wherein said activatable shield includes,
      i) a second tubular member with a second diameter having a second closed end and a second open end larger than said first diameter, said second tubular member made from a low Z material and having at least one portion provided with a substantially high Z substance deposited thereon, and
      ii) means for moving said first and second tubular members axially relative to each other,
   wherein said first open end is provided into said second open end such that said first and second tubular members form a substantially closed inner capsule in which said substantially high Z substance on said second tubular member is in a substantially non-overlapping configuration with said radioactive isotope on said first tubular member such that said radiation is transmitted through said second tubular member, and
   further wherein when said means for moving moves said first and second tubular member axially relative to each other, said at least one portion provided with said high Z substance on said second tubular member at least partially overlaps said at least one portion provided with said radioactive isotope on said first tubular member to thereby reduce the emission of radiation by said device.

10. An implantable brachytherapy device according to claim 9, wherein:
    said means for moving said first and second tubular members axially relative to each other is a gas provided in said substantially closed inner capsule which increases in pressure when said energy is applied to said device and forces said first and second tubular members axially relative to each other.

11. An implantable brachytherapy device according to claim 9, further comprising:
    f) a stop which prevents the relative axial movement of said first and second tubular members.

12. An implantable brachytherapy device according to claim 9, wherein:
    said at least one portion provided with said high Z substance is a plurality of portions provided with said high Z substance, and said at least one portion provided with said radioactive isotope is a plurality of portions provided with said radioactive isotope.

13. An implantable brachytherapy device according to claim 6, wherein:
    said activatable shield comprises a substantially radiopaque portion of a plurality of shape memory members, each of said plurality of shape memory members also having a portion upon which said isotope is provided, said plurality of shape memory members arranged in said container such that said portion having said isotope is directed to emit radiation through said container without substantial interference from said substantially radiopaque portions,
    wherein said plurality of said shape memory members include a predisposition to at least one of bend, rotate, and twist upon application of said energy such that said substantially radiopaque portions of said plurality of shape memory members at least partially surround said isotope.

14. An implantable brachytherapy device according to claim 13, wherein:
    said shape memory members include a predisposition to at least one of bend, rotate, and twist such that said substantially radiopaque portions of said plurality of shape memory members substantially surround said isotope.

15. An implantable brachytherapy device according to claim 13, wherein:
    said shape memory members are each in the form of an elongate rod and comprised of a substantially radiopaque material, and said isotope is provided along of longitudinal portion of each said shape memory member.

16. An implantable brachytherapy device according to claim 15, wherein:
    said shape memory members are each in the form of a longitudinal strip having first and second sides, each being bent along a longitudinal axis over said first side, said first side being provided with a substantially radiopaque material and said second side being provided with said radioactive isotope,
    wherein upon application of said energy said members at least partially unbend about said longitudinal axis such that said substantially radiopaque material at least partially blocks emission of radiation by said device.

17. An implantable brachytherapy device according to claim 6, further comprising:
    d) an inner capsule provided in said container, said inner capsule having a surface, at least one opening, and defining an interior,
    wherein said isotope is provided on said surface of said inner capsule, and said activatable shield means is provided in said interior of said inner capsule.

18. An implantable brachytherapy device according to claim 17, wherein:
    said inner capsule includes at least one opening,
    and wherein said brachytherapy device further comprises,
    e) a means for moving said activatable shield means from said interior through said at least one opening and between said isotope and said container.

19. An implantable brachytherapy device according to claim 18, wherein:
    said means for moving is one of a spring element and a pressurized fluid.

20. An implantable brachytherapy device according to claim 19, wherein:
    said activatable shield means comprises a low melting point metal.

21. An implantable brachytherapy device according to claim 17, wherein:
    said activatable shield comprises high Z particles provided in a wax.

22. An implantable brachytherapy device according to claim 6, further comprising:
    d) a covering over said activatable shield, said covering having a surface on which said radioactive isotope is provided,
    said activatable shield adapted to melt upon application of said amount of energy, and said covering is at least one of elastic and heat-shrinkable, such that when said amount of energy is applied to said device, said activatable shield melts and said covering forces said melted activatable shield from said cover to at least partially surround said radioactive isotope.

23. An implantable brachytherapy device, comprising:
   a) a biocompatible outer capsule having a wall adapted to transmit radiation therethrough;
   b) a radiopaque shield located inside said outer capsule; and
   c) a radioactive isotope located inside said outer capsule, wherein when said device is in a first state, said radioactive isotope emits radiation which is transmitted through said outer capsule, and
   wherein upon application of a predetermined amount of energy to said device said device enters into a second state in which said radiopaque shield at least partially surrounds said radioactive isotope and reduces the amount of radiation transmitted through said outer capsule.

24. An implantable brachytherapy device according to claim 23, wherein:
   said radioactive isotope is located between said shield and said wall when said device is in said first state.

25. An implantable brachytherapy device according to claim 23, further comprising:
   d) an inner capsule provided in said outer capsule, said inner capsule having a surface, and at least one opening, and defining an interior,
   wherein said isotope is provided on said surface of said inner capsule, and said shield is provided in said interior of said inner capsule.

26. An implantable brachytherapy device according to claim 25, wherein:
   said radiopaque shield comprises a low melting point metal.

27. An implantable brachytherapy device according to claim 26, further comprising:
   e) a means for moving said low melting point metal from said interior through said at least one opening and between said isotope and said wall of said outer capsule upon melting of said low melting point metal.

28. An implantable brachytherapy device according to claim 27, wherein:
   said means for moving is one of a spring element and a pressurized fluid.

29. An implantable brachytherapy device according to claim 26, wherein:
   said metal eutectic is one of a bismuth alloy, an indium alloy, a solder, and a eutectic metal alloy.

30. An implantable brachytherapy device according to claim 25, wherein:
   said radiopaque shield comprises high Z particles provided in a wax.

31. An implantable brachytherapy device according to claim 25, wherein:
   said radiopaque shield is a relatively high Z material which is in a liquid state at body temperature, and said brachytherapy device further comprises,
   e) a means for preventing said radiopaque shield from flowing through said at least one opening when said device is in said first state.

32. An implantable brachytherapy device according to claim 31, wherein:
   said means for preventing comprises a meltable plug which melts upon application of said predetermined amount of energy.

33. An implantable brachytherapy device according to claim 25, wherein:
   said inner capsule is held coaxial in said outer capsule.

34. An implantable brachytherapy device according to claim 23, further comprising:
   d) a covering over said radiopaque shield, said covering having a surface on which said isotope is provided,
   said radiopaque shield adapted to melt upon application of said predetermined amount of energy, and said covering is at least one of elastic and heat-shrinkable, such that when said predetermined amount of energy is applied to said device, said radiopaque shield melts and said covering forces said melted radiopaque shield from said cover to at least partially surround said isotope.

* * * * *